US00PP29036P2

(12) United States Plant Patent
Horvath

(10) Patent No.: US PP29,036 P2
(45) Date of Patent: Feb. 27, 2018

(54) ***SEDUM* PLANT NAMED 'ROCK STAR'**

(50) Latin Name: ***Sedum* hybrid**
Varietal Denomination: Rock Star

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 77 days.

(21) Appl. No.: 14/998,467

(22) Filed: Jan. 8, 2016

(51) Int. Cl.
*A01H 5/02* (2006.01)

(52) U.S. Cl.
USPC ..... Plt./479

(58) Field of Classification Search
USPC ..... Plt./479
CPC ..... A01H 5/02; A01H 5/12; A01H 5/00
See application file for complete search history.

(56) References Cited

PUBLICATIONS

American Nurseryman New Plants 2016: Intrinsic Perrennial Gardens Inc. 2015, retrieved on May 23, 2017, retrieved from the Internet at <http://www.amerinursery.com/plants/new-plants-2016-intrinsic-perennial-gardens-inc/> 9 pp.*

* cited by examiner

*Primary Examiner* — June Hwu

(57) ABSTRACT

A new, distinct *Sedum* plant as shown and described, characterized by pointed foliage, pink flowers and a larger height.

2 Drawing Sheets

Latin name: *Sedum* hybrid.
Cultivar name: 'Rock Star'.

BACKGROUND OF THE INVENTION

The present invention relates to a new and distinct hybrid of *Sedum* plant named 'Rock Star' characterized by pointed or fingered foliage, pink flowers and a larger height compared to the seed parent. The new *Sedum* was raised as a seedling from open pollinated seed sown as an unnamed *Sedum tatarinowii*, not patented, in Hebron, Ill. in 2013. The selection of the new plant was due to its' larger pointed foliage, larger pink flowers and a taller height compared to the seed parent. Initial asexual reproduction has taken place at a nursery in Hebron, Ill. since 2014 by means of division, and vegetative stem cuttings. The new *Sedum* has shown to be stable and identical in reproduction to the parent after rooting over 700 plants from 2014 to 2015.

SUMMARY OF THE INVENTION

The new *Sedum* plant named 'Rock Star' characterized by pointed foliage, pink flowers and a larger height compared to the seed parent have been observed to be unique and stable.

Plants of the new *Sedum* can be compared to plants of *Sedum spectabile* 'Neon' not patented. 1. The new *Sedum* plant is a hybrid and does not produce seed while *Sedum spectabile* 'Neon' is fertile and produces seed. 2. The new *Sedum* plant has a mature size measuring 25 cm high and 45 cm wide while *Sedum spectabile* 'Neon' measures 45 cm high and 45 cm wide. 3. The new *Sedum* has pink flowers while *Sedum spectabile* 'Neon' has a deeper pink flower color.

Plants of the new *Sedum* can also be compared to the seed parent plant *Sedum tatarinowii*, not patented. 1. The new plant is a hybrid and does not produce seed while the seed parent plant is fertile and produces viable seed. 2. The new *Sedum* has a mature size measuring 25 cm high and 45 cm while the seed parent has a mature size of 12 cm high and 30 cm wide. 3. The new *Sedum* has larger foliage measuring on average up to 2 cm across by 4 cm long while the seed parent has foliage measuring 6mm across by 2 cm long. 4. The new *Sedum* has a stem thickness of 9-10 mm while the seed parent has stem thickness of 2 mm.

DESCRIPTION OF PHOTOGRAPHS

Figure 1:
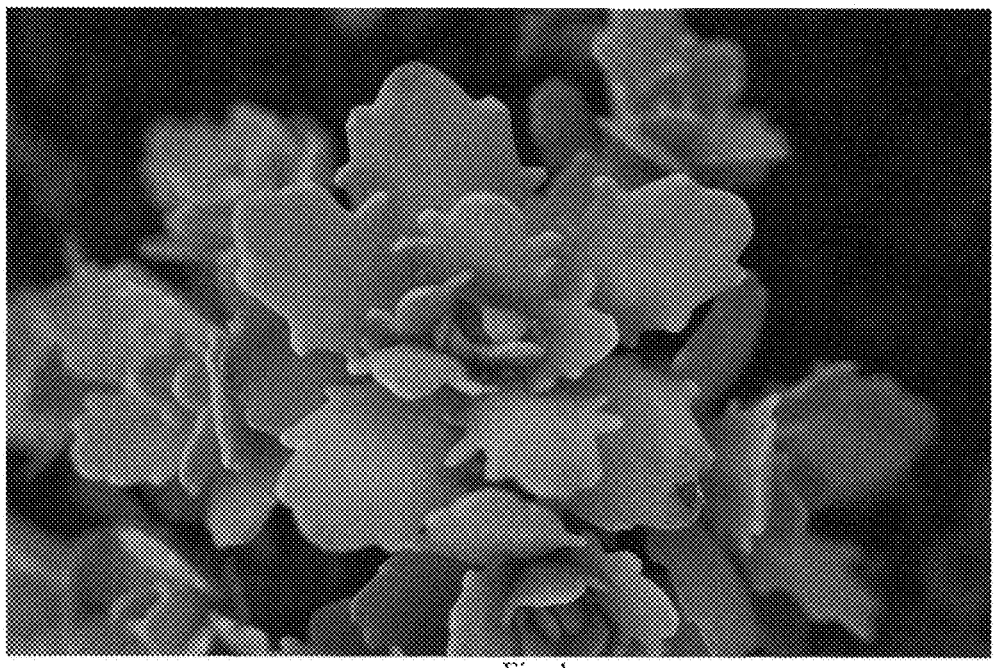
Figure 2:
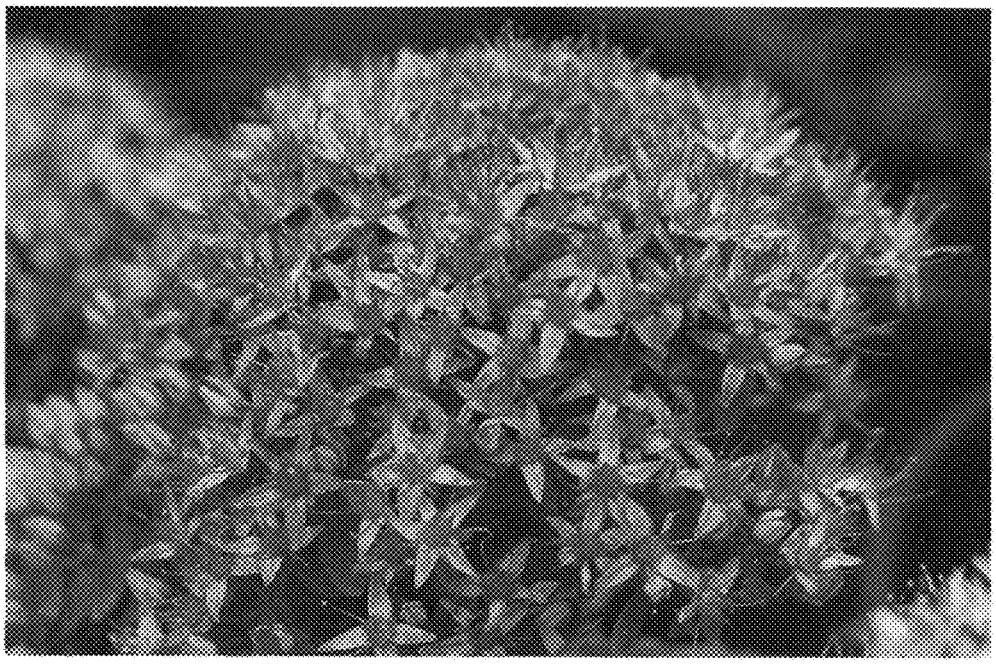
Figure 3:
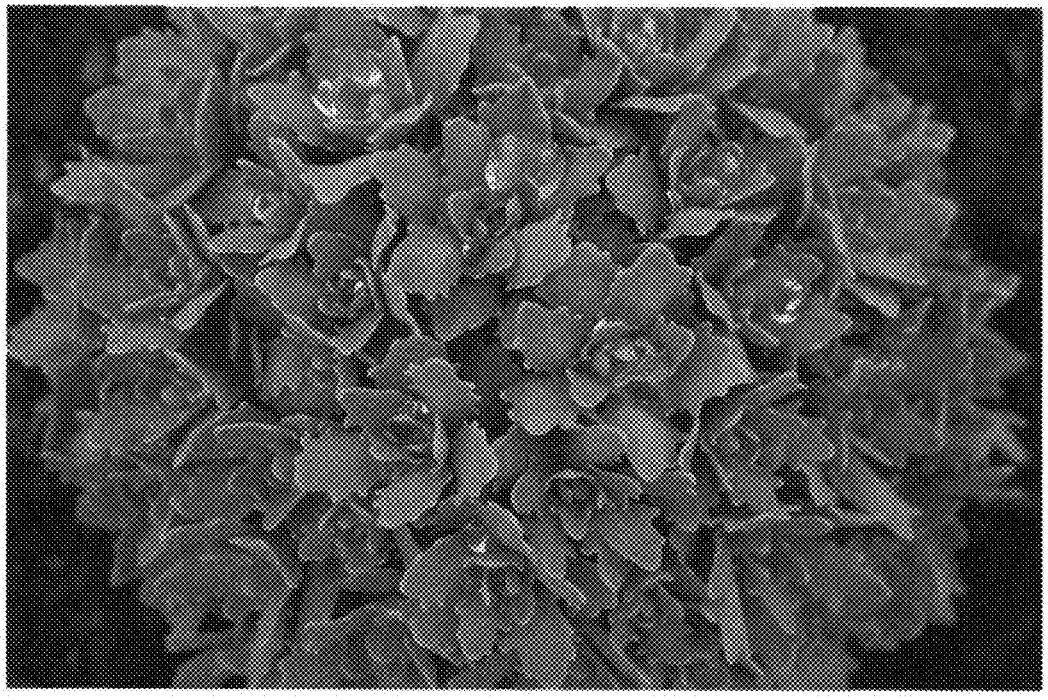

Plants pictured in the drawing were grown for three years.
FIG. 1. Close up of the foliage.
FIG. 2. Close up of the flower.
FIG. 3. A single plant in Spring.

DETAILED BOTANICAL DESCRIPTION

In the following description, color references are made to The Royal Horticultural Society Colour Chart (2001). Plants used for the description were grown for three years. Measurements and numerical values represent averages of typical plants.

Botanical classification: *Sedum* hybrid cultivar Rock Star.

Parentage: Male or pollen unknown and female or seed an open pollinated, unknown *Sedum tatarinowii.*

Propagation: Vegetative division and stem cutting propagation.

Plant description: Overall habit of the new *Sedum* is basal clumps, with uptight stems topped by pink flowers in August and September.

*Plant height.*—Average 25 cm.

*Plant width.*—45 cm.

*Stem color.*—152 B in spring and summer, maturing 199 A in September and 184 A near the flower.

*Stem shape*.—Both typical and observed — round.
*Stem texture*.—Glabrous.
*Stem length*.—25 cm.
*Stem diameter*.—9-10 mm.
*Internode length*.—5 cm.

Foliage:
*Type*.—Deciduous.
*Shape*.—Obovate.
*Petiole*.—None.
*Length*.—4 cm and.
*Width*.—2 cm.
*Thickness*.—1-2 mm.
*Margin*.—Coarsely and irregularly toothed.
*Leaf apex, typical and observed*.—Obtuse.
*Leaf bases, typical and observed*.—Cuneate.
*Texture*.—Smooth on both the upper and lower surface.
*Leaf arrangement*.—Alternate, crowded except at the base of the stems.
*Leaf venation pattern*.—None noticed.
*Leaf vein color*.—None noticed.
*Adaxial leaf description*.—Color is 137 A.
*Abaxial leaf description*.—Color is 137 B.
*Fall foliage color*.—None noticed.

Flower:
*Petal count*.—5.
*Petal shape*.—Lanceolate.
*Adaxial petal color*.—75 A.
*Abaxial petal color*.—Edged in pink 75 A, with some green 157 A in the center and some white 155 C too.
*Petal apex shape*.—Acuminate.
*Petal base*.—3 mm wide.
*Petal length*.—6 mm.
*Petal width*.—3 mm.
*Petal margin, typical and observed*.—Entire.
*Petal bases, typical and observed*.—Obtuse.
*Inflorescence type*.—Panicle on basal flowering stems.
*Panicle colors*.—Petals 75 A and carpel N74 A.
*Individual flower size*.—13 mm across, 6 mm tall.
*Inflorescence length and width*.—10 cm.
*Flower number*.—Approximately 500 per stem.
*Bloom period and duration*.—Mid August to Mid September.
*Bud shape, typical and observed*.—Elliptical.
*Bud length, typical and observed*.—4 mm.
*Bud diameter, typical and observed*.—3 mm.
*Bud colors, typical and observed*.—N74 A at the tip, N74 C in the center, 150 D at the base.
*Sepal size*.—1 mm across, 2 mm tall.
*Sepal number*.—5.
*Sepal shape, typical and observed*.—Narrow ovate.
*Sepal apex, typical and observed*.—Acute.
*Sepal margin, typical and observed*.—Entire.
*Sepal color, abaxial and adaxial typical and observed*.—Close to 138 D.
*Peduncle length, typical and observed*.—15 mm.
*Peduncle diameter, typical and observed*.—1 mm.
*Peduncle color, typical and observed*.—Close to 139 A.
*Pedicel length, typical and observed*.—2 mm.
*Pedicel diameter, typical and observed*.—1 mm.
*Pedicel color, typical and observed*.—Close to 139 A.
*Carpel color*.—N74 A.
*Carpel surfaces*.—Glabrous.
*Average number of carpels per individual flower*.—5.
*Stigma shape*.—Capitate.
*Stigma size*.—2 mm.
*Stigma color*.—Close to N74 A.
*Style length*.—1 mm.
*Style shape*.—Slender.
*Style color*.—N74 A.
*Ovary size*.—1-2 mm.
*Ovary shape*.—Cordate.
*Ovary color*.—N74 A.
*Fertility*.—Sterile, 10 anthers no pollen, 10 stamens.
*Anther color*.—Close to N187 C.
*Pollen color*.—Close to 21 B.
*Blooming habit*.—Domed, terminal panicle on up to 25 cm stems.
*Scent*.—No scent noticed.
*Fruit*.—None.
*Hardiness*.—U.S.D.A. hardiness zones 4-9.
*Disease resistance*.—Resistance to *Rhizoctonia* a fungus disease common to *Sedum* has been observed on plants grown under nursery conditions.
*Pest resistance*.—Resistance to pests common to *Sedum* has not been observed on plants grown under nursery conditions.

I claim:

1. A new, distinct *Sedum* plant as shown and described, characterized by pointed foliage, pink flowers and a larger height compared to the seed parent.

* * * * *